(12) United States Patent
Mihara (10) Patent No.: US 9,017,677 B2
(45) Date of Patent: Apr. 28, 2015

(54) METHODS OF TREATING A DISEASE MEDIATED BY SENSITIZED T CELLS

(75) Inventor: Masahiko Mihara, Gotenba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 1282 days.

(21) Appl. No.: 11/340,412

(22) Filed: Jan. 25, 2006

(65) Prior Publication Data

US 2006/0134113 A1 Jun. 22, 2006

Related U.S. Application Data

(63) Continuation of application No. 09/381,598, filed as application No. PCT/JP98/01217 on Mar. 20, 1998, now abandoned.

(30) Foreign Application Priority Data

Mar. 21, 1997 (JP) ........................................ 9-68467

(51) Int. Cl.
| | | |
|---|---|---|
| *A61K 39/395* | (2006.01) | |
| *A61K 39/00* | (2006.01) | |
| *C12P 21/08* | (2006.01) | |
| *C07K 16/28* | (2006.01) | |
| *C07K 16/30* | (2006.01) | |
| *C07K 16/24* | (2006.01) | |

(52) U.S. Cl.
CPC ......... *C07K 16/248* (2013.01); *A61K 2039/505* (2013.01); *C07K 16/2866* (2013.01)

(58) Field of Classification Search
None
See application file for complete search history.

(56) References Cited

U.S. PATENT DOCUMENTS

| | | | |
|---|---|---|---|
| 5,134,142 A | 7/1992 | Matsuo et al. | |
| 5,171,840 A | 12/1992 | Kishimoto | |
| 5,210,075 A | 5/1993 | Scholz et al. | |
| 5,480,796 A | 1/1996 | Kishimoto | |
| 5,605,930 A | 2/1997 | Samid | |
| 5,670,373 A | 9/1997 | Kishimoto | |
| 5,795,965 A | 8/1998 | Tsuchiya et al. | |
| 5,817,790 A | 10/1998 | Tsuchiya et al. | |
| 5,851,793 A | 12/1998 | Kishimoto | |
| 5,888,510 A | 3/1999 | Kishimoto et al. | |
| 5,948,820 A | 9/1999 | Fujita et al. | |
| 5,990,282 A | 11/1999 | Kishimoto | |
| 6,086,874 A | 7/2000 | Yoshida et al. | |
| 6,261,560 B1 | 7/2001 | Tsujinaka et al. | |
| 6,406,909 B1 | 6/2002 | Shibuya et al. | |
| 6,410,691 B1 | 6/2002 | Kishimoto | |
| 6,428,979 B1 | 8/2002 | Kishimoto | |
| 6,537,782 B1 | 3/2003 | Shibuya et al. | |
| 6,692,742 B1 | 2/2004 | Nakamura et al. | |
| 6,723,319 B1 | 4/2004 | Ito et al. | |
| 6,875,432 B2 | 4/2005 | Liu et al. | |
| 6,962,812 B2 | 11/2005 | Shibuya et al. | |
| 7,320,792 B2 | 1/2008 | Ito et al. | |
| 7,332,289 B2 | 2/2008 | Takeda et al. | |
| 7,479,543 B2 | 1/2009 | Tsuchiya et al. | |
| 7,498,031 B2 | 3/2009 | Fujioka et al. | |
| 7,521,052 B2 | 4/2009 | Okuda et al. | |
| 7,566,453 B2 | 7/2009 | Nakamura et al. | |
| 7,666,413 B2 | 2/2010 | Liu et al. | |
| 7,771,723 B2 | 8/2010 | Nakamura et al. | |
| 7,824,674 B2 | 11/2010 | Ito et al. | |
| 7,927,815 B2 | 4/2011 | Takeda et al. | |
| 7,955,598 B2 | 6/2011 | Yoshizaki et al. | |
| 8,017,121 B2 | 9/2011 | Kishimoto et al. | |
| 8,142,776 B2 | 3/2012 | Liu et al. | |
| 8,173,126 B2 | 5/2012 | Yoshizaki et al. | |
| 8,227,195 B2 | 7/2012 | Stubenrauch et al. | |
| 8,398,980 B2 | 3/2013 | Kano et al. | |
| 8,420,789 B2 | 4/2013 | Takeda et al. | |
| 8,440,196 B1 | 5/2013 | Funakoshi et al. | |
| 8,470,316 B2 | 6/2013 | Yasunami | |
| 8,529,895 B2 | 9/2013 | Mihara et al. | |
| 8,530,176 B2 | 9/2013 | Stubenrauch et al. | |
| 8,562,990 B2 | 10/2013 | Ito et al. | |
| 8,562,991 B2 | 10/2013 | Igawa et al. | |
| 8,568,720 B2 | 10/2013 | Morichika et al. | |
| 8,580,264 B2 | 11/2013 | Zhang et al. | |
| 8,597,644 B2 | 12/2013 | Ito et al. | |
| 8,617,550 B2 | 12/2013 | Nishimoto et al. | |
| 8,623,355 B2 | 1/2014 | Okada et al. | |
| 8,632,778 B2 | 1/2014 | Kakuta et al. | |
| 8,709,409 B2 | 4/2014 | Okuda et al. | |
| 8,734,800 B2 | 5/2014 | Kano et al. | |

(Continued)

FOREIGN PATENT DOCUMENTS

| | | |
|---|---|---|
| CA | 2001790 | 4/1990 |
| EP | 0617126 | 9/1994 |

(Continued)

OTHER PUBLICATIONS

Tamura T et al. Soluble interleukin-6 receptor triggers osteoclast formation by interleukin-6. Proc. Natl. Acad. Sci. USA. 1993, vol. 90, p. 11924-11928.*

Sato K et al. Reshaping a human antibody to inhibit the interleukin 6-dependent tumor cell growth. Cancer Research. 1993, vol. 53, p. 851-856).*

Okazaki M, et al. Characterization of anti-mouse interleukin-6 receptor antibody. Immunology Letters. 2002. vol. 84, p. 231-240.*

Leung, D.Y.M. Mechanisms controlling the human immunoglobulin E response: New directions in the therapy of allergic diseases. Pediatric Research, 1992, vol. 33 (Suppl), No. 1, p. S56-S62.*

(Continued)

*Primary Examiner* — Robert Landsman
*Assistant Examiner* — Bruce D Hissong
(74) *Attorney, Agent, or Firm* — Morrison & Foerster LLP (57) ABSTRACT

A preventive or therapeutic agent for sensitized T cell-mediated diseases comprising an interleukin-6 (IL-6) antagonist, for example an antibody directed against IL-6 receptor, an antibody directed against IL-6, an antibody directed against gp130, and the like.

20 Claims, 1 Drawing Sheet

(56) References Cited

U.S. PATENT DOCUMENTS

| | | |
|---|---|---|
| 8,771,686 B2 | 7/2014 | Ishida |
| 8,809,509 B2 | 8/2014 | Takeda et al. |
| 8,840,884 B2 | 9/2014 | Kakuta et al. |
| 2002/0187150 A1 | 12/2002 | Mihara et al. |
| 2004/0115197 A1 | 6/2004 | Yoshizaki et al. |
| 2005/0118163 A1 | 6/2005 | Mizushima et al. |
| 2005/0158303 A1 | 7/2005 | Liu et al. |
| 2005/0238644 A1 | 10/2005 | Mihara et al. |
| 2006/0127975 A1 | 6/2006 | Link et al. |
| 2006/0165696 A1 | 7/2006 | Okano et al. |
| 2006/0292147 A1 | 12/2006 | Yoshizaki et al. |
| 2007/0036785 A1 | 2/2007 | Kishimoto et al. |
| 2007/0053900 A1 | 3/2007 | Liu et al. |
| 2007/0086995 A1 | 4/2007 | Liu et al. |
| 2007/0134242 A1 | 6/2007 | Nishimoto et al. |
| 2008/0124761 A1 | 5/2008 | Goto et al. |
| 2008/0274106 A1 | 11/2008 | Nishimoto et al. |
| 2008/0306247 A1 | 12/2008 | Mizushima et al. |
| 2009/0022719 A1 | 1/2009 | Mihara et al. |
| 2009/0061466 A1 | 3/2009 | Hoesel et al. |
| 2009/0131639 A1 | 5/2009 | Kakuta et al. |
| 2009/0220500 A1 | 9/2009 | Kobara |
| 2009/0269335 A1 | 10/2009 | Nakashima et al. |
| 2009/0280129 A1 | 11/2009 | Liu et al. |
| 2009/0291076 A1 | 11/2009 | Morichika et al. |
| 2010/0008907 A1 | 1/2010 | Nishimoto et al. |
| 2010/0061986 A1 | 3/2010 | Takahashi et al. |
| 2010/0129355 A1 | 5/2010 | Ohguro et al. |
| 2010/0158898 A1 | 6/2010 | Liu et al. |
| 2011/0117087 A1 | 5/2011 | Franze et al. |
| 2011/0150869 A1 | 6/2011 | Mitsunaga et al. |
| 2011/0206664 A1 | 8/2011 | Yoshizaki et al. |
| 2011/0245473 A1 | 10/2011 | Igawa et al. |
| 2011/0262462 A1 | 10/2011 | Platt et al. |
| 2012/0009177 A1 | 1/2012 | Platt et al. |
| 2012/0064086 A1 | 3/2012 | Liu et al. |
| 2012/0076783 A1 | 3/2012 | Liu et al. |
| 2012/0183539 A1 | 7/2012 | Maeda |
| 2012/0253016 A1 | 10/2012 | Igawa et al. |
| 2013/0149302 A1 | 6/2013 | Mitsunaga et al. |
| 2013/0202588 A1 | 8/2013 | Nishimura |
| 2013/0317203 A1 | 11/2013 | Igawa et al. |
| 2014/0005367 A1 | 1/2014 | Morichika et al. |
| 2014/0017236 A1 | 1/2014 | Okuda et al. |
| 2014/0056883 A1 | 2/2014 | Zhang et al. |
| 2014/0056884 A1 | 2/2014 | Zhang et al. |
| 2014/0056885 A1 | 2/2014 | Zhang et al. |
| 2014/0079695 A1 | 3/2014 | Nishimoto et al. |

FOREIGN PATENT DOCUMENTS

| | | |
|---|---|---|
| EP | 0628639 | 12/1994 |
| EP | 0 783 893 | 7/1997 |
| EP | 0 983 767 | 9/2008 |
| JP | 3-141261 | 6/1991 |
| JP | 03-232485 | 10/1991 |
| JP | 03-291236 | 12/1991 |
| JP | 04-169538 | 6/1992 |
| JP | 05-211888 | 8/1993 |
| JP | 7-502977 | 3/1995 |
| JP | 07-324097 | 12/1995 |
| JP | 8-99902 | 4/1996 |
| JP | 08-208514 | 8/1996 |
| JP | 9-511745 | 11/1997 |
| JP | 11-507354 | 6/1999 |
| JP | 2003-334068 | 11/2003 |
| JP | 3630453 | 12/2004 |
| JP | 3822137 | 6/2006 |
| JP | 2009-092508 | 4/2009 |
| WO | WO-92/21367 | 12/1992 |
| WO | WO-95/10271 | 4/1995 |
| WO | WO-95/27499 | 10/1995 |
| WO | WO-96/06068 | 2/1996 |
| WO | WO-96/11020 | 4/1996 |
| WO | WO-96/40230 | 12/1996 |
| WO | WO-97/24340 | 7/1997 |
| WO | WO-00/10607 | 3/2000 |
| WO | WO-02/13859 | 2/2002 |
| WO | WO-2008/016134 | 2/2008 |
| WO | WO-2008/078715 | 7/2008 |
| WO | WO-2011/149046 | 12/2011 |
| WO | WO-2011/149051 | 12/2011 |
| WO | WO-2013/031237 | 3/2013 |

OTHER PUBLICATIONS

Kleiner G.I. et al. Suppressiosn of human IgE antibody forming cell responses by IL-6. J. Leukocyte Biology, 1993, vol. 54, p. 168-170.*
Brown et al., Adv. Dermatol. (1989) 4:1-28.
Abstract of Japan No. 69 C 923, Abstract No. 3-291236.
Beers and Berkow (eds.), The Merck Manual of Diagnosis and Therapy, 17th ed., (1999) pp. 1475-1477.
Gijbels et al., Mol. Med. (1995) 1(7):795-805.
International Search Report dated Jun. 16, 1998.
Mihara et al., Eur. J. Immunol. (1991) 21:2327-2331.
Sato, Cancer Research (1993) 53:851-856.
Suen et al., J. Exp. Med. 1997 186:1233-1240.
Vink et al., J. Exp. Med. (1990) 172:997-1000.
Wendling et al., The Journal of Rheumatology (1993) 20:259-262.
Toshitani et al., J. of Investigative Dermatology (1993) 3:299-304.
Canadian Office Action for CA 2,284,271, mailed Jun. 4, 2007, 4 pages.
Jayaraman et al., J. Immunol. (1990) 144:942-951.
Summons to Attend Oral Proceedings for EP application No. 98909796.9-2402, dated Oct. 2, 2007.
Pashov et al., Cytokines, Medline Accession No. NLM9291172, Apr. 1997 (Abstract).
European Search Report for EP 08002163.7, mailed Dec. 2, 2008, 7 pages.
Rodgriguez et al., The Journal of Immunology (1994) 153(8):3811-3821.
Gornikiewicz et al., FASEB J (2000) 14:1093-1100.
Ulich et al., American Journal of Pathology (1991) 138(5):1097-1101.
Communication of a Notice of Opposition filed in European Patent No. 2,011,514, dated Dec. 3, 2012.
De Vos et al. (1992) "Cytokines and Uveitis, a Review," Current Eye Research 11(6):581-597.
Guice et al. (1991) "Anti-Tumor Necrosis Factor Antibody Augments Edema Formation in Caerulein-Induced Acute Pancreatitis," Journal of Surgical Research 51(6):495-499.
Hocking et al. (1990) "Mechanisms of Pulmonary Edema Induced by Tumor Necrosis Factor-$\alpha$," Circulation Research 67(1):68-77.
Hoekzema et al. (1990) "Cytokines and Intraocular Inflammation," Current Eye Research 9:207-211.
Hoekzema et al. (1991) "Analysis of Interleukin-6 in Endotoxin-Induced Uveitis," Investigative Opthalmology & Visual Science 32(1): 88-95.
Hoekzema et al. (1992) "Endotoxin-Induced Uveitis in the Rat," Investigative Opthalmology & Visual Science 33(3):532-539.
Murray et al. (1990) "Aqueous Humor Interleukin-6 Levels in Uveitis," Investigative Opthalmology & Visual Science 31(5):917-920.
Murray (1991) "Abstracts of the 31st Meeting of the Association for Eye Research," Documenta Opthalmologica 77:91-151.
Caspi et al., "Mouse models of experimental autoimmune uveitis," Ophthalmic Res (2008) 40:169-174.
Gery and Streilein, "Autoimmunity in the eye and its regulation," Curr Opin Immunol (1994) 6(6):938-945.
Leung, "Mechanisms controlling the human immunoglobulin E response: new directions in the therapy of allergic diseases," (1993) 33(1 Suppl):S56-S62.
Meisler et al., "Anterior uveitis and multiple sclerosis," Cleve Clin J Med (1989) 56(5):535-538.
Porter, "Uveitis in association with multiple sclerosis," Br J Ophthal (1972) 56:478-481.

(56) References Cited

OTHER PUBLICATIONS

Final Written Submissions of the Opponent, dated Jul. 16, 2014, filed in European Patent Office Opposition Proceedings to European Patent No. 2011514, 5 pages.
Allergenic Diseases and Autoimmune Diseases, Wikipedia, English and Japanese versions of Wikipedia entry, dated Jun. 17, 2013, 4 pages.
Bellomo, "The Cytokine Network in the Critically Ill," Anaesthesia and Intensive Care (1992) 20(3):288-302.
EU Clinical Trials Register regarding "Sarilumab", dated Jul. 11, 2014, 4 pages.
Ogata et al., "Anti-IL-6 receptor antibody does not ameliorate radiation pneumonia in mice," Experimental and Therapeutic Medicine (2012) 4:273-276.
Ogata et al., "Early administration of IL-6RA does not prevent radiation-induced lung injury in mice," Radiation Oncology (2010) 5:26, 6 pages.
Pope et al., "Delayed Type Hypersensitivity in Patients with Rheumatoid Arthritis," The Journal of Rheumatology (1993) 20:17-20.
Rinsho Kensa (Clinical Test) (including translation) (1991) 35(5):447-452.
Sarilumab entry from Wikipedia, dated Jul. 14, 2014.
U.S. Appl. No. 08/414,425, filed Mar. 31, 1995.
U.S. Appl. No. 14/241,567, filed Aug. 31, 2012.
U.S. Appl. No. 14/201,346, filed Mar. 7, 2014.
U.S. Appl. No. 14/252,648, filed Apr. 14, 2014.
U.S. Appl. No. 14/329,487, filed Jul. 11, 2014.
U.S. Appl. No. 14/495,001, filed Sep. 24, 2014.
U.S. Appl. No. 14/520,423, filed Oct. 22, 2014.
Website of Japanese Clinic (including translation) regarding autoimmune versus allergenic diseases, dated Jun. 17, 2013, 2 pages.

* cited by examiner

METHODS OF TREATING A DISEASE MEDIATED BY SENSITIZED T CELLS

TECHNICAL FIELD

The present invention relates to a preventive or therapeutic agent for sensitized T cell-mediated diseases comprising an interleukin-6 (IL-6) antagonist as an active ingredient. The present invention also relates to an inhibitor of sensitized T cells comprising an interleukin-6 (IL-6) antagonist as an active ingredient. Furthermore, the present invention relates to a suppressive agent of sensitized T cells comprising an antibody directed against IL-6 receptor as an active ingredient.

BACKGROUND ART

IL-6 is a cytokine which is also called B cell stimulating factor 2 (BSF2) or interferon β2. IL-6 was discovered as a differentiation factor involved in the activation of B-lymphatic cells (Hirano, T. et al., Nature (1986) 324, 73-76). Thereafter, it was found to be a multifunctional cytokine that influences various functions of cells (Akira, S. et al., Adv. in Immunology (1993) 54, 1-78). IL-6 has been reported to induce the. maturation of T-lymphatic cells (Lotz et al., J. Exp. Immunol. 18: 1253-1258, 1988).

IL-6 transmits its biological activity through two types of proteins on the cell. One of them is IL-6 receptor, a ligand-biding protein with a molecular weight of about 80 kD, to which IL-6 binds. IL-6 receptor occurs not only in a membrane-bound form that penetrates through and is expressed on the cell membrane but also as a soluble IL-6 receptor consisting mainly of the extracellular region.

The other protein is a membrane-bound protein gp130 having a molecular weight of about 130 kD that is involved in signal transduction. IL-6 and IL-6 receptor form the IL-6/IL-6 receptor complex which, after binding to gp130, transmits its biological activity to the cell (Taga, T. et al., J. Exp. Med. (1987) 166, 967).

IL-6 antagonist is a substance that inhibits the transduction of biological activity of IL-6. As the IL-6 antagonist, there have been known so far antibody directed against IL-6 (anti-IL-6 antibody), antibody directed against IL-6 receptor (anti-IL-6 receptor antibody), and antibody directed against gp130 (anti-gp130 antibody). In addition, there are also known IL-6 antagonists that are disclosed in the International Patent Application WO 95-00852, the International Patent Application WO 95-11303, the International Patent Application WO 96-34104, the International Patent Application WO 96-18648, the International Patent Application WO 96-17869, Japanese Unexamined Patent Publication (Kokai). No. 7(1995)-324097, and Japanese Unexamined Patent Publication (Kokai) No. 8(1996)-311098.

Anti-IL-6 receptor antibody has been described in several reports (Novick D. et. al., Hybridoma (1991) 10, 137-146, Huang, Y. W. et al., Hybridoma (1993) 12, 621-630, International Patent Application WO 95-09873, French Patent Application FR 2694767, U.S. Pat. No. 521,628). A humanized PM-1 antibody was obtained by grafting the complementarity determining regions (CDRs) of a mouse antibody PM-1 (Hirata et al., J. Immunology (1989) 143, 2900-2906), to a human antibody (the International Patent Application WO 92-19759).

On the other hand, in many autoimmune diseases and allergic diseases, there are T cells that recognize specific antigens (sensitized T cells) and these sensitized T cells are known to be involved in the pathology of such diseases. For example, there are known the presence of sensitized T cells that are directed to myelin basic protein in multiple sclerosis (Zhang, J. et al., J. Exp. Med (1994) 179, 973-984), S antigen in uveitis (Nussenblatt, R. B. et al., Am. J. Ophthalmol (1980) 89, 173-179), thyroglobulin in chronic thyroiditis, foods and acarids for atopic dermatitis (Kubota, Y. et al., J. Dermatol (1993) 20, 85-87, Kondo, N. et al., J. Allergy Clin. Immunol (1993) 91, 658-668), bacteria, viruses, fungi, etc. in delayed hypersensitivity, and metal, Japanese lacquer, etc. in contact dermatitis, and the like.

Furthermore, it is also possible to induce pathological states similar to those in humans by immunizing an animal with these antigens or by introducing antigen-specific sensitized T cells into a non-immunized animal. Based on these facts, it is thought that sensitized T cells play an important role in the above diseases. Currently, steroids and/or immunosuppressive agents are used for the treatment of these diseases, but they are symptomatic treatments and require administration for a long period of time, which eventually poses the problem of side effects.

It has not been known so far that IL-6 antagonists as described above exhibit a suppressive effect on sensitized T cells and a therapeutic effect on the diseases in which sensitized T cells are involved.

DISCLOSURE OF THE INVENTION

It is an object of the present invention to provide a therapeutic agent for sensitized T cell-mediated diseases said agent being free of the above-mentioned drawbacks.

Thus, the present invention relates to a preventive or therapeutic agent for sensitized T cell-mediated diseases comprising an IL-6 antagonist as an active ingredient.

The present invention also relates to a preventive or therapeutic agent for sensitized T cell-mediated diseases comprising an antibody directed against IL-6 receptor as an active ingredient.

The present invention also relates to a preventive or therapeutic agent for sensitized T cell-mediated diseases comprising a monoclonal antibody directed against IL-6 receptor as an active ingredient.

The present invention also relates to a preventive or therapeutic agent for sensitized T cell-mediated diseases comprising a monoclonal antibody directed against human IL-6 receptor as an active ingredient.

The present invention also relates to a preventive or therapeutic agent for sensitized T cell-mediated diseases comprising a monoclonal antibody directed against mouse IL-6 receptor as an active ingredient.

The present invention also relates to a preventive or therapeutic agent for sensitized T cell-mediated diseases comprising PM-1 antibody as an active ingredient.

The present invention also relates to a preventive or therapeutic agent for sensitized T cell-mediated diseases comprising MR16-1 antibody as an active ingredient.

The present invention also relates to a preventive or therapeutic agent for sensitized T cell-mediated diseases comprising an antibody directed against IL-6 receptor having the constant region (C region) of human antibody as an active ingredient.

The present invention also relates to a preventive or therapeutic agent for sensitized T cell-mediated diseases comprising a chimeric antibody or a humanized antibody directed against IL-6 receptor as an active ingredient.

The present invention also relates to a preventive or therapeutic agent for sensitized T cell-mediated diseases comprising humanized PM-1 antibody as an active ingredient.

The present invention also relates to a preventive or therapeutic agent for multiple sclerosis, uveitis, chronic thyroiditis, delayed hypersensitivity, contact dermatitis, or atopic dermatitis comprising the above IL-6 antagonist as an active ingredient.

The present invention also relates to an suppressive agent of sensitized T cells comprising IL-6 antagonist as an active ingredient.

The present invention also relates to an suppressive agent of sensitized T cells comprising an antibody directed against IL-6 receptor as an active ingredient.

EMBODIMENT FOR CARRYING OUT THE INVENTION

1. IL-6 Antagonist

IL-6 antagonists for use in the present invention may be of any origin, any kind, and any form, as long as they have a suppressive effect on sensitized T cells, a preventive or therapeutic effect for diseases in which sensitized T cells are involved.

IL-6 antagonists block signal transduction by IL-6 and inhibit the biological activity of IL-6. As the IL-6 antagonist, there can be mentioned anti-IL-6 antibody, anti-IL-6 receptor antibody, anti-gp130 antibody, altered IL-6, or partial peptides of IL-6 or IL-6 receptor.

1-1. Anti-IL-6 Antibody

Anti-IL-6 antibodies for use in the present invention can be obtained as polyclonal or monoclonal antibodies using a known method. As the anti-IL-6 antibodies for use in the present invention, monoclonal antibodies of, in particular, a mammalian origin, are preferred. Monoclonal antibodies of a mammalian origin include those produced by a hybridoma and recombinant antibody produced by a host which has been transformed with an expression vector containing genetically engineered antibody genes. These antibodies, via binding to IL-6, inhibit the binding of IL-6 to IL-6 receptor, and thereby blocks signal transduction of the biological activity of IL-6 into the cell.

Examples of such antibodies include MH166 (Matsuda et al., Eur. J. Immunol. (1988) 18, 951-956) and SK2 antibody (Sato, K. et al., The 21st Nihon Mennekigakkai Soukai (General Meeting of the Japan Immunology Society), Academic Record (1991) 21, 166) and the like.

1-1-1. Preparation of IL-6

An anti-IL-6 antibody-producing hybridoma can be basically constructed using a known procedure as described below. Thus, IL-6 may be used as a sensitizing antigen and is immunized in the conventional method of immunization. The immune cells thus obtained are fused with known parent cells in the conventional cell fusion process, and then monoclonal antibody-producing cells are screened by the conventional screening method to prepare the desired hybridoma.

Specifically, anti-IL-6 antibody may be obtained in the following manner. For example, a human antigen used as the sensitizing antigen can be obtained using the IL-6 gene sequence/amino acid sequence disclosed in Eur. J. Biochem (1987) 168, 543, J. Immunol. (1988) 140, 1534, or Argic. Biol. (1990) 54, 2685.

After a suitable host cell was transformed by inserting the IL-6 gene sequence into a known expression vector system, the IL-6 protein of interest is purified from the host cell or the culture supernatant thereof. The purified IL-6 protein can be used as a sensitizing antigen. Alternatively, a fusion protein of the IL-6 protein and another protein may be used as a sensitizing antigen.

1-2. Anti-IL-6 Receptor Antibody

Anti-IL-6 receptor antibodies for use in the present invention can be obtained as polyclonal or monoclonal antibodies using a known method. As the anti-IL-6 antibodies for use in the present invention, monoclonal antibodies of, in particular, a mammalian origin, are preferred. Monoclonal antibodies of a mammalian origin include those produced by a hybridoma and those produced by a host which has been transformed with an expression vector containing genetically engineered antibody genes. The antibodies, via binding to IL-6 receptor, inhibit the binding of IL-6 to IL-6 receptor, and thereby block the transduction of the biological activity of IL-6 into the cell.

Examples of such antibodies include MR16-1 antibody (Saito, et al., J. Immunology (1993) 147, 168-173), PM-1 antibody (Hirata, et al., J. Immunology (1989) 143, 2900-2906), or AUK12-20 antibody, AUK64-7 antibody or AUK146-15 antibody (International Patent Application, WO 92-19759), and the like. Among them, PM-1 antibody is most preferred.

Incidentally, the hybridoma cell line which produces PM-1 antibody has been internationally deposited under the provisions of the Budapest Treaty as PM-1 on Jul. 10, 1990 with the National Institute of Bioscience and Human Technology, Agency of Industrial Science and Technology, of 1-3, Higashi 1-chome, Tsukuba-shi, Ibaraki, Japan, as FERM BP-2998. And the hybridoma cell line which produces MR16-1 antibody has been internationally deposited under the provisions of the Budapest Treaty as Rat-mouse hybridoma MR16-1 on Mar. 13, 1997 with the National Institute of Bioscience and Human Technology, Agency of Industrial Science and Technology, of 1-3, Higashi 1-chome, Tsukuba-shi, Ibaraki, Japan, as FERM BP-5875.

1-2-1. Preparation of IL-6 Receptor

Hybridomas producing a monoclonal antibody can be basically prepared using a known procedure as described bellow. Thus, IL-6 receptor is used as a sensitizing antigen and is immunized according to the conventional method of immunization. The immune cells thus obtained are fused with known parent cells in the conventional cell fusion process, and then monoclonal antibody-producing cells may be screened by the conventional screening method to prepare the desired hybridoma.

Specifically, anti-IL-6 receptor antibody may be prepared in the following manner. For example, the human IL-6 receptor used as the sensitizing antigen for obtaining antibody can be obtained using the IL-6 receptor gene sequence/amino acid sequence disclosed in European Patent Application EP 325474, and the mouse IL-6 receptor can be obtained using that disclosed in Japanese Unexamined Patent Publication (Kokai) 3(1991)-155795.

There are two types of IL-6 receptor proteins: IL-6 receptor expressed on the cell membrane, and IL-6 receptor detached from the cell membrane (soluble IL-6 Receptor) (Yasukawa et al., J. Biochem. (1990) 108, 673-676). Soluble IL-6 receptor antibody is composed substantially of the extracellular region of the IL-6 receptor bound to the cell membrane, and thereby is different from the membrane-bound IL-6 receptor in that the latter lacks the transmembrane region or both of the transmembrane region and the intracellular region.

After the gene sequence of IL-6 receptor was inserted into a known expression vector system to transform an appropriate host cell, the desired IL-6 receptor protein may be purified from the host cell or a culture supernatant thereof using a known method. The IL-6 receptor protein thus purified may be used as the sensitizing antigen. Alternatively, cells that are expressing IL-6 receptor protein or a fusion protein of the IL-6 receptor protein and another protein may be used as the sensitizing antigen.

E. coli that has a plasmid pIBIBSF2R containing cDNA encoding human IL-6 receptor has been internationally deposited under the provisions of the Budapest Treaty as HB101-pIBIBSF2R on Jan. 9, 1989. with the National Institute of Bioscience and Human Technology, Agency of Industrial Science and Technology, of 1-3, Higashi 1-chome, Tsukuba-shi, Ibaraki, Japan, as FERM BP-2232.

1-3. Anti-gp130 Antibody

Anti-gp130 antibodies for use in the present invention can be obtained as polyclonal or monoclonal antibodies using a known method. As the anti-gp130 antibodies for use in the present invention, monoclonal antibodies of, in particular, a mammalian origin, are preferred. Monoclonal antibodies of a mammalian origin include those produced by a hybridoma and those produced by a host which has been transformed with an expression vector containing genetically engineered antibody genes. The antibodies, via binding to gp130, inhibit the binding of IL-6/IL-6 receptor complex to gp130, and thereby block the transduction of the biological activity of IL-6 into the cell.

Examples of such antibodies include AM64 antibody (Japanese unexamined Patent Publication (Kokai) 3(1991)-219894), 4B11 antibody and 2H4 antibody (U.S. Pat. No. 5,571,513), B-S12 antibody and B-P8 antibody (Japanese Unexamined Patent Publication (Kokai) 8(1996)-291199).

1-3-1. Preparation of gp130

A monoclonal antibody-producing hybridoma can be basically constructed using a known procedure as described below. Thus, gp130 may be used as a sensitizing antigen and is immunized in the conventional method of immunization. The immune cells thus obtained are fused with known parent cells in the conventional cell fusion process, and then the monoclonal antibody-producing hybridomas are screened by the conventional screening method to prepare the desired hybridoma.

Specifically, monoclonal antibody may be obtained in the following manner. For example, gp130 used as the sensitizing antigen can be obtained using the IL-6 receptor gene sequence/amino acid sequence disclosed in European Patent Application EP 411946.

After a suitable host cell was transformed by inserting the gp130 gene sequence into a known expression vector system, the gp130 protein of interest is purified from the host cell or from the culture supernatant thereof. The purified gp130 protein can be used as the sensitizing antigen. Alternatively, cells that are expressing IL-6 receptor protein or a fusion protein of the gp130 protein and another protein may be used as the sensitizing antigen.

1-4. Preparation of Antibody-Producing Hybridoma

Though mammals to be immunized with the sensitizing antigen are not specifically limited, they are preferably selected in consideration of their compatibility with the parent cell for use in cell fusion. They generally include, but not limited to, rodents such as mice, rats, hamsters and the like.

Immunization of animals with a sensitizing antigen is carried out using a known method. A general method, for example, involves the intraperitoneal or subcutaneous administration of a sensitizing antigen to the mammal. Specifically, a sensitizing antigen which has been diluted and suspended in an appropriate amount of phosphate buffered saline (PBS) or physiological saline etc. is mixed, as desired, with an appropriate amount of a common adjuvant, for example Freund's complete adjuvant. After being emulsified, it is preferably administered to a mammal for several times every 4 to 21 days. Alternatively a suitable carrier may be used at the time of immunization of the sensitizing antigen.

After immunization and the confirmation of the increase in the desired antibody levels in the serum, the immune cells are taken out from the mammal and are subjected to cell fusion, in which preferred immune cells include, in particular, the spleen cells.

The mammalian myeloma cells as the other parent cells which are subjected to cell fusion with the above-mentioned immune cells preferably include various known cell lines such as P3X63Ag8.653) (J. Immunol. (1979) 123: 1548-1550), P3X63Ag8U.1 (Current Topics in Microbiology and Immunology (1978) 81: 1-7), NS-1 (Kohler, G. and Milstein, C., Eur. J. Immunol. (1976) 6: 511-519), MPC-11 (Margulies, D. H. et al., Cell (1976) 8: 405-415), SP2/0 (Shulman, M. et al., Nature (1978) 276: 269-270), FO (de St. Groth, S. F. et al., J. Immunol. Methods (1980) 35: 1-21), S194 (Trowbridge, I. S., J. Exp. Med. (1978) 148: 313-323), R210 (Galfre, G. et al., Nature (1979) 277: 131-133) and the like.

Cell fusion between the above immune cells and the myeloma cells may be essentially conducted in accordance with a known method such as is described in Milstein et al. (Kohler, G. and Milstein, C., Methods Enzymol. (1981) 73: 3-46) and the like.

More specifically, the above cell fusion is carried out in the conventional nutrient broth in the presence of, for example, a cell fusion accelerator. As the cell fusion accelerator, for example, polyethylene glycol (PEG), Sendai virus (HVJ) and the like may be used, and, in addition, an adjuvant such as dimethyl sulfoxide etc. may be added as desired to enhance efficiency of the fusion.

The preferred ratio of the immune cells and the myeloma cells to be used is, for example, 1 to 10 times more immune cells than the myeloma cells. Examples of culture media to be used for the above cell fusion include RPMI1640 medium and MEM culture medium suitable for the growth of the above myeloma cell lines, and the conventional culture medium used for this type of cell culture, and besides a serum supplement such as fetal calf serum (FCS) may be added.

In cell fusion, predetermined amounts of the above immune cells and the myeloma cells are mixed well in the above culture liquid, to which a PEG solution previously heated to about 37° C., for example a PEG solution with a mean molecular weight of about 1000 to 6000, is added at a concentration of 30 to 60% (w/v) and mixed to obtain the desired fusion cells (hybridomas). Then by repeating the sequential addition of a suitable culture liquid and centrifugation to remove the supernatant, cell fusion agents etc., which are undesirable for the growth of the hybridoma, can be removed.

Said hybridoma is selected by culturing in the conventional selection medium, for example, the HAT culture medium (a culture liquid containing hypoxanthine, aminopterin, and thymidine). Culturing in said HAT culture medium is continued generally for a period of time sufficient to effect killing of the cells other than the desired hybridoma (non-fusion cells), generally several days to several weeks. The conventional limiting dilution method is conducted in which the hybridomas that produce the desired antibody are screened and monclonally cloned.

In addition to obtaining the above hybridoma by immunizing an animal other than the human with an antigen, it is also possible to sensitize human lymphocytes in vitro with desired antigen or desired antigen-expressing cells, and the resulting sensitized B lymphocytes are fused with a human myeloma cell, for example U266, to obtain the desired human antibody having the activity of binding to desired antigen or desired antigen-expressing cells (see Japanese Post-examined Patent Publication (Kokoku) No. 1(1989)-59878). Furthermore, a transgenic animal having a repertoire of all human antibody genes is immunized with the antigen or the antigen-expressing cells to obtain the desired human antibody in the method described above (see International Patent Application WO 93/12227, WO 92/03918, WO 94/02602, WO 94/25585, WO 96/34096 and WO 96/33735).

The monoclonal antibody-producing hybridomas thus constructed can be subcultured in the conventional culture liquid, or can be stored for a prolonged period of time in liquid nitrogen.

In order to obtain monoclonal antibodies from said hybridoma, there can be mentioned a method in which said hybridoma is cultured in the conventional method and the antibodies are obtained as the supernatant, or a method in which the hybridoma is administered to and grown in a mammal compatible with said hybridoma and the antibodies are obtained as the ascites. The former method is suitable for obtaining high-purity antibodies, whereas the latter is suitable for a large scale production of antibodies.

Specifically the hybridoma producing anti-IL-6 receptor antibody can be constructed using the method disclosed in Japanese Unexamined Patent Publication (Kokai) 3(1989)-139293. It can be conducted by a method in which the PM-1 antibody-producing hybridoma that was internationally deposited under the provisions of the Budapest Treaty as FERM BP-2998 on Jul. 10, 1990 with the National Institute of Bioscience and Human Technology, Agency of Industrial Science and Technology, of 1-3, Higashi 1-chome, Tsukuba-shi, Ibaraki, Japan, is intraperitoneally injected to BALB/c mice (manufactured by CLEA Japan) to obtain the ascites from which the PM-1 antibody is purified, or: a method in which said hybridoma is cultured in a suitable culture medium such as the RPMI1640 medium containing 10% bovine fetal serum and 5% BM-Condimed H1 (manufactured by Boehringer Mannheim), the hybridoma SFM medium (manufactured by GIBCO-BRL), the PFHM-II medium (manufactured by GIBCO-BRL) and the like, and the PM-1 antibody can be purified from the supernatant.

1-5. Recombinant Antibody

A recombinant antibody which was produced by the recombinant gene technology in which an antibody gene was cloned from the hybridoma and integrated into a suitable vector which was then introduced into a host can be used in the present invention as monoclonal antibody (see, for example, Carl, A. K., Borrebaeck, and James, W. Larrick, THERAPEUTIC MONOCLONAL ANTIBODIES, published in the United Kingdom by MACMILLAN PUBLISHERS LTD. 1990).

Specifically, mRNA encoding the variable (V) region of the desired antibody is isolated from the hybridoma producing the antibody. The isolation of mRNA is conducted by preparing total RNA using, for example, a known method such as the guanidine ultracentrifuge method (Chirgwin, J. M. et al., Biochemistry (1979) 18, 5294-5299), the AGPC method (Chmczynski, P. et al., (1987) 162, 156-159), and then mRNA is purified from the total RNA using the mRNA Purification kit (manufactured by Pharmacia) and the like. Alternatively, mRNA can be directly prepared using the Quick Prep mRNA Purification Kit (manufactured by Pharmacia).

cDNA of the V region of antibody may be synthesized from the mRNA thus obtained using a reverse transcriptase. cDNA may be synthesized using the AMV Reverse Transcriptase First-strand cDNA Synthesis Kit and the like. Alternatively, for the synthesis and amplification of cDNA, the 5'-Ampli FINDER RACE Kit (manufactured by Clontech) and the 5'-RACE method (Frohman, M. A. et al., Proc. Natl. Acad. Sci. U.S.A. (1988) 85, 8998-9002; Belyavsky, A. et al., Nucleic Acids Res. (1989) 17, 2919-2932) that employs polymerase chain reaction (PCR) may be used. The desired DNA fragment is purified from the PCR product obtained and may be ligated to vector DNA. Moreover, a recombinant vector is constructed therefrom and then is introduced into E. coli etc., from which colonies are selected to prepare the desired recombinant vector. The base sequence of the desired DNA may be confirmed by a known method such as the dideoxy method.

Once the DNA encoding the V region of the desired antibody has been obtained, it may be ligated to DNA encoding the constant region (C region) of the desired antibody, which is then integrated into an expression vector. Alternatively, the DNA encoding the V region of the antibody may be integrated into an expression vector which already contains DNA encoding the C region of the antibody.

In order to produce the antibody for use in the present invention, the antibody gene is integrated as described below into an expression vector so as to be expressed under the control of the expression regulatory region, for example an enhancer and/or a prompter. Subsequently, the expression vector may be transformed into a host cell and the antibody can then be expressed therein.

1-6. Altered Antibody

In accordance with the present invention, artificially altered recombinant antibody such as chimeric antibody and humanized antibody can be used for the purpose of lowering heterologous antigenicity against humans. These altered antibody can be produced using known methods.

Chimeric antibody can be obtained by ligating the thus obtained DNA encoding the V region of antibody to DNA encoding the C region of human antibody, which is then integrated into an expression vector and introduced into a host for production of the antibody therein (see European Patent Application EP 125023, and International Patent Application WO 96/02576). Using this known method, chimeric antibody useful for the present invention can be obtained.

For example, the plasmid that contains DNA encoding the L chain V region or the H chain V region of chimeric PM-1 antibody was designated as pPM-k3 or pPM-h1, respectively, and E. coli having the plasmid has been internationally deposited under the provisions of the Budapest Treaty as NCIMB 40366 and NCIMB 40362, respectively, on Feb. 11, 1991 with the National Collections of Industrial and Marine Bacteria Limited (see International Patent Application WO 92-19759).

Humanized antibody which is also called reshaped human antibody has been made by grafting the complementarity determining regions (CDRs) of antibody of a mammal other than the human, for example mouse antibody, into the CDRs of a human antibody. The general recombinant DNA technology for preparation of such antibodies is also known (see European Patent Application EP 125023 and International Patent Application WO 96/02576).

Specifically, a DNA sequence which was designed to ligate the CDR of mouse antibody with the framework region (FR)

of human antibody is synthesized from several divided oligonucleotides having sections overlapping with one another at the ends thereof by the PCR technique. The DNA thus obtained is ligated to the DNA encoding the C region of human antibody and then is integrated into an expression vector, which is introduced into a host for antibody production (see European Patent Application EP 239400 and International Patent Application WO 92-19759).

For the FR of human antibody ligated through CDR, the complementarity determining region that forms a favorable antigen binding site is selected. When desired, amino acids in the framework region of the antibody variable region may be substituted so that the complementarity determining region of reshaped human antibody may form an appropriate antigen biding site (Sato, K. et al., Cancer Res. (1993) 53, 851-856).

For chimeric antibody or humanized antibody, the C region of human antibody is used. As the C region of human antibody, there can be mentioned Cγ, and Cγ1, Cγ2, Cγ3, and Cγ4, for example, can be used. The C region of human antibody may be modified to improve the stability of antibody or the production thereof.

Chimeric antibody consists of the variable region of antibody derived from a mammal other than the human and the C region derived from human antibody, whereas humanized antibody consists of the complementarity determining region of antibody derived from a mammal other than the human and the framework region (FR) and the C region of antibody derived from human antibody. Accordingly, antigenicity thereof in the human body has been reduced so that they are useful as the active ingredient of the therapeutic agents of the present invention.

A preferred embodiment of the humanized antibody for use in the present invention includes humanized PM-1 antibody (see International Patent Application WO 92-19759).

1-7. Expression and Production

Antibody genes constructed as described above may be expressed and obtained in a known method. In the case of mammalian cells, expression may be accomplished using a DNA in which a commonly used useful promoter, the antibody gene to be expressed, and the poly A signal at 3' downstream thereof have been operably linked or a vector containing said DNA. Examples of the promoter/enhancer include human cytomegalovirus immediate early promoter/enhancer.

Additionally, as the promoter/enhancer which can be used for expression of antibody for use in the present invention, there are viral promoters/enhancers such as retrovirus, polyoma virus, adenovirus, and simian virus 40 (SV40), and promoters/enhancers derived from mammalian cells such as human elongation factor la (HEF1α).

For example, expression may be readily accomplished by the method of Mulligan et al. (Nature (1979) 277, 108) when SV40 promoter/enhancer is used, or by the method of Mizushima et al. (Nucleic Acids Res. (1990) 18, 5322) when HEF1α promoter/enhancer is used.

In the case of E. coli, expression may be conducted by operably linking a commonly used useful promoter, a signal sequence for antibody secretion, and the antibody gene to be expressed, followed by expression thereof. As the promoter, for example, there can be mentioned lacz promoter and araB promoter. The method of Ward et al. (Nature (1098) 341, 544-546; FASEB J. (1992) 6, 2422-2427) may be used when lacz promoter is used, and the method of Better et al. (Science (1988) 240, 1041-1043) may be used when araB promoter is used.

As the signal sequence for antibody secretion, when produced in the periplasm of E. coli, the pelB signal sequence (Lei, S. P. et al., J. Bacteriol. (1987) 169, 4379) can be used.

After separating the antibody produced in the periplasm, the structure of the antibody is appropriately refolded before use (see, for example, WO 96/30394).

As the origin of replication, there can be used those derived from SV40, polyoma virus, adenovirus, bovine papilloma virus (BPV) and the like. Furthermore, for the amplification of the gene copy number in the host cell system, expression vectors can include as selectable markers the aminoglycoside transferase (APH) gene, the thymidine kinase (TK) gene, E. coli xanthine guaninephosphoribosyl transferase (Ecogpt) gene, the dihydrofolate reductase (dhfr) gene and the like.

For the production of antibody for use in the present invention, any production system can be used. The production system of antibody preparation comprises the in vitro or the in vivo production system. As the in vitro production system, there can be mentioned a production system which employs eukaryotic cells and the production system which employs prokaryotic cells.

When the eukaryotic cells are used, there are the production systems which employ animal cells, plant cells, and fungal cells. Known animal cells include (1) mammalian cells such as CHO cells, COS cells, myeloma cells, baby hamster kidney (BHK) cells, HeLa cells, and Vero cells, (2) amphibian cells such as *Xenopus* oocytes, or (3) insect cells such as sf9, sf21, and Tn5. Known plant cells include, for example, those derived from *Nicotiana tabacum*, which is subjected to callus culture. Known fungal cells include yeasts such as the genus *Saccharomyces*, more specifically *Saccharomyces cerevisiae*, or filamentous fungi such as the genus *Aspergillus*, more specifically *Aspergillus niger*.

When the prokaryotic cells are used, there are the production systems which employ bacterial cells. Known bacterial cells include *Escherichia coli* (*E. coli*), and *Bacillus subtilis*.

By introducing via transformation the gene of the desired antibody into these cells and culturing the transformed cells in vitro, the antibody can be obtained. Culturing is conducted in the known methods. For example, as the culture liquid, DMEM, MEM, RPMI1640, and IMDM can be used, and serum supplements such as fetal calf serum (FCS) may be used in combination. In addition, antibodies may be produced in vivo by implanting cells into which the antibody gene has been introduced into the abdominal cavity of an animal and the like.

As in vivo production systems, there can be mentioned those which employ animals and those which employ plants. When animals are used, there are the production systems which employ mammals and insects.

As mammals, goats, pigs, sheep, mice, and cattle can be used (Vicki Glaser, SPECTRUM Biotechnology Applications, 1993). Also, as insects, silkworms can be used.

When plants are used, tabacco, for example, can be used.

Antibody genes are introduced into these animals or plants, and the antibodies are produced in such animals or plants, and recovered. For example, an antibody gene is inserted into the middle of the gene encoding protein which is inherently produced in the milk such as goat β casein to prepare fusion genes. DNA fragments containing the fusion gene into which the antibody gene has been inserted are injected into a goat embryo, and the embryo is introduced into a female goat. The desired antibody is obtained from the milk produced by the transgenic goat born to the goat who received the embryo or offsprings thereof. In order to increase the amount of milk containing the desired antibody produced by the transgenic goat, hormones may be given to the transgenic goat as appropriate. (Ebert, K. M. et al., Bio/Technology (1994) 12, 699-702).

When silkworms are used, baculovirus into which the desired antibody gene has been inserted is infected to the silkworm, and the desired antibody can be obtained from the body fluid of the silkworm (Susumu, M. et al., Nature (1985) 315, 592-594). Moreover, when tabacco is used, the desired antibody gene is inserted into an expression vector for plants, for example pMON 530, and then the vector is introduced into a bacterium such as *Agrobacterium tumefaciens*. The bacterium is then infected to tabacco such as *Nicotiana tabacum* to obtain the desired antibody from the leaves of the tabacco (Julian, K.-C. Ma et al., Eur. J. Immunol. (1994) 24, 131-138).

When antibody is produced in in vitro or in vivo production systems, as described above, DNA encoding the heavy chain (H chain) or the light chain (L chain) of antibody may be separately integrated into an expression vector and the hosts are transformed simultaneously, or DNA encoding the H chain and the L chain may be integrated into a single expression vector and the host is transformed therewith (see International Patent Application WO 94-11523).

1-8. Modified Antibody

Antibodies for use in the present invention may be antibody fragments or modified versions thereof as long as they are preferably used. For example, as fragments of antibody, there may be mentioned Fab, F(ab')2, Fv or single-chain Fv (scFv) in which Fv's of H chain and L chain were ligated via a suitable linker. Specifically antibodies are treated with an enzyme, for example, papain or pepsin, to produce antibody fragments, or genes encoding these antibody fragments are constructed, and then introduced into an expression vector, which is expressed in a suitable host cell (see, for example, Co, M. S. et al., J. Immunol. (1994) 152, 2968-2976; Better, M. and Horwitz, A. H., Methods in Enzymology (1989) 178, 476-496, Academic Press, Inc.; Plueckthun, A. and Skerra, A., Methods in Enzymology (1989) 178, 476-496, Academic Press, Inc.; Lamoyi, E., Methods in Enzymology (1986) 121, 652-663; Rousseaux, J. et al., Methods in Enzymology (1986) 121, 663-669; Bird, R. E. et al., TIBTECH (1991) 9, 132-137).

scFv can be obtained by ligating the V region of H chain and the V region of L chain of antibody. In the scFv, the V region of H chain and the V region of L chain are preferably ligated via a linker, preferably a peptide linker (Huston, J. S. et al., Proc. Natl. Acad. Sci. U.S.A. (1988) 85, 5879-5883). The V region of H chain and the V region of L chain in the scFv may be derived from any of the above-mentioned antibodies. As the peptide linker for ligating the V regions, any single-chain peptide comprising, for example, 12-19 amino acid residues may be used.

DNA encoding scFv can be obtained using DNA encoding the H chain or the H chain V region of the above antibody and DNA encoding the L chain or the L chain V region of the above antibody as the template by amplifying the portion of the DNA encoding the desired amino acid sequence among the above sequences by the PCR technique with the primer pair specifying the both ends thereof, and by further amplifying the combination of DNA encoding the peptide linker portion and the primer pair which defines that both ends of said DNA be ligated to the H chain and the L chain, respectively.

Once DNAs encoding scFv are constructed, an expression vector containing them and a host transformed with said expression vector can be obtained by the conventional methods, and scFv can be obtained using the resultant host by the conventional methods.

These antibody fragments can be produced by obtaining the gene thereof in a similar manner to that mentioned above and by allowing it to be expressed in a host. "Antibody" as used in the claim of the present application encompasses these antibody fragments.

As modified antibodies, antibodies associated with various molecules such as polyethylene glycol (PEG) can be used. "Antibody" as used in the claim of the present application encompasses these modified antibodies. These modified antibodies can be obtained by chemically modifying the antibodies thus obtained. These methods have already been established in the art.

1-9. Separation and Purification of Antibody 1-9-1. Separation and Purification of Antibody Antibodies produced and expressed as described above can be separated from the inside or outside of the host cell and then may be purified to homogeneity. Separation and purification of the antibody for use in the present invention may be accomplished by affinity chromatography. As the column used for such affinity chromatography, there can be mentioned Protein A column and Protein G column. Examples of the carriers used in the Protein A column are Hyper D, POROS, Sepharose F. F. and the like. Alternatively, methods for separation and purification conventionally used for proteins can be used without any limitation. Separation and purification of the antibody for use in the present invention may be accomplished by combining, as appropriate, chromatography other than the above-mentioned affinity chromatography, filtration, ultrafiltration, salting-out, dialysis and the like. Chromatography includes, for example, ion exchange chromatography, hydrophobic chromatography, gel-filtration and the like. These chromatographies can be applied into HPLC. Alternatively, reverse-phase chromatography can be used.

1-9-2. Determination of Antibody Concentration

The concentration of antibody obtained in the above 2-1 can be determined by the measurement of absorbance or by the enzyme-linked immunosorbent assay (ELISA) and the like. Thus, when absorbance measurement is employed, the antibody for use in the present invention or a sample containing the antibody is appropriately diluted with PBS(-) and then the absorbance is measured at 280 nm, followed by calculation using the absorption coefficient of 1.35 OD at 1 mg/ml. When the ELISA method is used, measurement is conducted as follows. Thus, 100 µl of goat anti-human IgG (manufactured by TAGO) diluted to 1 µg/ml in 0.1 M bicarbonate buffer, pH 9.6, is added to a 96-well plate (manufactured by Nunc), and is incubated overnight at 4° C. to immobilize the antibody.

After blocking, 100 µl each of appropriately diluted antibody for use in the present invention or a sample containing the antibody, or 100 µl of human IgG (manufactured by CAPPEL) as the standard is added, and. incubated at room temperature for 1 hour. After washing, 100 µl of 5000-fold diluted alkaline phosphatase-labeled anti-human IgG antibody (manufactured by BIO SOURCE) is added, and incubated at room temperature for 1 hour. After washing, the substrate solution is added and incubated, followed by the measurement of absorbance at 405 nm using the MICROPLATE READER Model 3550 (manufactured by Bio-Rad) to calculate the concentration of the desired antibody.

1-10. IL-6 Antagonists Other Than Antibodies

The altered IL-6 for use in the present invention has an activity of binding to IL-6 receptor and does not transmit the biological activity of IL-6. Thus, the altered IL-6, though it competes with IL-6 for binding to IL-6 receptor, does not transmit the biological activity of IL-6, and thereby it blocks signal transduction by IL-6.

Altered IL-6 may be constructed through the introduction of mutation by replacing amino acid residues of the amino 
acid sequence of IL-6. IL-6, the source of the altered IL-6, may be of any origin, but when the antigenicity is to be considered, it is preferably human IL-6. Specifically, the secondary structure of IL-6 is predicted using a known molecular modeling program of the amino acid sequence, for example WHATIF (Vriend et al., J. Mol. Graphics (1990), 8, 52-56), and the overall effects of the amino acid residue to be replaced is evaluated. After an appropriate amino acid residue was determined, mutation is introduced by the commonly used polymerase chain reaction (PCR) method using a vector containing the base sequence encoding human IL-6 gene thereby to obtain a gene encoding altered IL-6. This is then integrated, as desired, into an appropriate expression vector, from which altered IL-6 can be obtained according to the expression, production and purification of said recombinant antibody.

Specific examples of the altered IL-6 are disclosed in Brakenhoff et al., J. Biol. Chem. (1994) 269, 86-93, and Savino et al., EMBO J. (1994) 13, 1357-1367, WO 96-18648, and WO 96-17869.

The IL-6 partial peptide or the IL-6 receptor partial peptide for use in the present invention has an activity of binding to IL-6 receptor or IL-6, respectively, and does not transmit the biological activity of IL-6. Thus, the IL-6 partial peptide or the IL-6 receptor partial peptide binds to IL-6 receptor or IL-6, respectively, and thereby capture it. As a result, they do not transmit the biological activity of IL-6, and block signal transduction of IL-6.

The IL-6 partial peptide or the IL-6 receptor partial peptide is a peptide comprising some or all of the amino acid sequence of the region involved in the binding to IL-6 and IL-6 receptor in the amino acid sequence of IL-6 or IL-6 receptor. Such a peptide generally comprises 10-80, preferably 20-50, more preferably 20-40 amino acid residues.

The IL-6 partial peptide or the IL-6 receptor partial peptide can be constructed by specifying the region involved in the binding to IL-6 and IL-6 receptor in the amino acid sequence of IL-6 or IL-6 receptor, and by producing some or all of the amino acid sequence by a conventional method such as a genetic engineering technology or a peptide synthesis method.

In order to prepare the IL-6 partial peptide or the IL-6 receptor partial peptide by a genetic engineering technology, the DNA sequence encoding the desired peptide is integrated into an expression vector, from which the peptide can be obtained according to the expression, production, and purification of said recombinant antibody.

Preparation of the IL-6 partial peptide or the IL-6 receptor partial peptide by the peptide synthesis method can be effected using a method commonly used in peptide synthesis such as the solid phase synthesis or the liquid phse synthesis. Specifically the method described in Zoku-iyakuhin no Kaihatsu (Sequel to Development of Pharmaceuticals), Vol. 14, Peputido Gousei (Peptide Synthesis), edited by Haruaki Yajima, Hirokawa Shoten, 1991, may be used. The solid phase synthesis method used includes, for example, a reaction in which an amino acid corresponding to the C-terminal of the peptide to be synthesized is coupled to a support which is insoluble in organic solvents, and then an amino acid in which α-amino group or a side chain functional group has been protected with an appropriate protecting group is condensed one amino acid at a time from the C-terminal to the N-terminal direction, and a reaction in which said protecting group of the α-amino group of the amino acid or the peptide coupled to the resin is eliminated is alternately repeated to elongate the peptide chain. The solid phase peptide synthesis methods are divided into the Boc method and the Fmoc method depending on the type of protecting group to be used.

After the synthesis of the desired peptide is complete, the peptide chain is cleaved from the support via a deprotection reaction. For cleavage from the peptide chain, hydrogen fluoride or trifuluoromethane sulfonate in the Boc method and TFA in the Fmoc method are generally used. In the Boc method, for example, the above peptide resin is treated in hydrogen fluoride in the presence of anisole. Subsequently, the protecting group is eliminated and the peptide is recovered by cleaving from the support. By lyopholizing this, crude peptide can be obtained. On the other hand, in the Fmoc method, TFA, for example, is used in a manner similar to the above to effect the deprotection reaction and the cleavage reaction of the peptide from the support.

The crude peptide thus obtained can be applied to HPLC for its separation and purification. Its elution can be carried out in a water-acetonitrile solvent system that is commonly used for protein purification under an optimum condition. The fraction corresponding to the peak of the profile of the chromatography obtained is collected and lyophilized. The peptide fraction thus purified is identified by subjecting it to the analysis of molecular weight by mass spectroscopic analysis, the analysis of amino acid composition, or the analysis of amino acid sequence, and the like.

Specific examples of the IL-6 partial peptide or the IL-6 receptor partial peptide are disclosed in Japanese Unexamined Patent Publication (Kokai) 2(1990)-188600, Japanese Unexamined Patent Publication (Kokai) 7(1995)-324097, Japanese Unexamined Patent Publication (Kokai) 8(1996)-311098, and U.S. Pat. No. 5,210,075.

2. Confirmation of the Activity of IL-6 Antagonist

The activity of the IL-6 antagonist for use in the present invention can be evaluated using a conventionally known method. For example, IL-6 is added to the IL-6-dependent cell MH60.BSF2 and the activity can be evaluated using the incorporation of $^{3}$H-thymidine into the IL-6-dependent cell in the coexistence of the IL-6 antagonist as an index. Alternatively, evaluation can be effected by adding $^{125}$I-labeled IL-6 and an excess amount of non-labled IL-6 to the U266, an IL-6 receptor-expressing cell, and adding the IL-6 antagonist at the same time and then by determining the $^{125}$I-labeled IL-6 bound to the IL-6 receptor-expressing cell.

3. Confirmation of Therapeutic Effects

In order to confirm the effects accomplished by the present invention, the IL-6 antagonist for use in the present invention may be given to an animal that has been sensitized with T cells via challenge or to an animal to which sensitized T cells have been introduced, and the suppressive effects on the sensitized T cells are evaluated.

As the sensitizing antigen to be given to the animal, for example, tubercle bacillus can be used.

As the animal to be immunized, animals generally used in the experiments can be used such as mice, rats, rabbits, and the like. The effect of the present invention to be evaluated can be confirmed by observing the delayed inflammatory reaction induced by challenging the same antigen to an animal that was given the antigen.

As described the examples below, in the mouse delayed foot pad edema reaction, the administration of anti-IL-6 receptor antibody resulted in suppression of the delayed inflammatory reaction was observed. Since it was known that sensitized T cells are involved in the delayed foot pad edema reaction, it was revealed that IL-6 antagonists such as anti-IL-6 receptor antibody exert an inhibitory effect on the sensitized T cells.

4. Route of Administration and Pharmaceutical Preparation

The preventive or therapeutic agents for sensitized T cell-mediated diseases of the present invention may be administered, either systemically or locally, by a parenteral route, for example intravenous injection such as drip infusion, intramuscular injection, intraperitoneal injection, and subcutaneous injection. The method of administration may be chosen, as appropriate, depending on the age and the conditions of the patient. The effective dosage is chosen from the range of 0.01 mg to 100 mg per kg of body weight per administration. Alternatively, the dosage in the range of 1 to 1000 mg, preferably 5 to 50 mg per patient may be chosen.

The preventive or therapeutic agents for sensitized T cell-mediated diseases of the present invention may contain pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like.

Additives used are chosen from, but not limited to, the above or combinations thereof depending on the dosage form.

The subject diseases to be prevented or treated of the present invention are diseases in which sensitized T cell are involved. Specifically, they include delayed hypersensitivity, chronic thyroiditis, uveitis, atopic dermatitis, contact dermatitis, or multiple sclerosis. The preventive or therapeutic agents of the present invention are useful as preventive or therapeutic agents for diseases in which these sensitized T cells are involved.

EXAMPLES

The present invention will now be explained in more details with reference to the working examples, reference examples, and experimental examples. It should be noted, however, that the present invention is not limited to them in any way.

Example 1

Inhibitory Effects on Delayed Foot Pad Reaction

Dry dead cells of *Mycobacterium butyricum* were added to 2.5 mg/ml in the Freund's incomplete adjuvant to prepare an emulsion, 0.2 ml of which was then subcutaneously injected to C57BL/6 male mice for challenge. On day 14, 10 mg of dry dead cells of *Mycobacterium butyricum* suspended in physiological saline were subcutaneously injected to the right foot pad of the animal to evoke the reaction. Twenty four hours later, the weights of the left and the right foot pad were measured and the difference in the weights were used as an index of the strength of the reaction.

Figure 1:
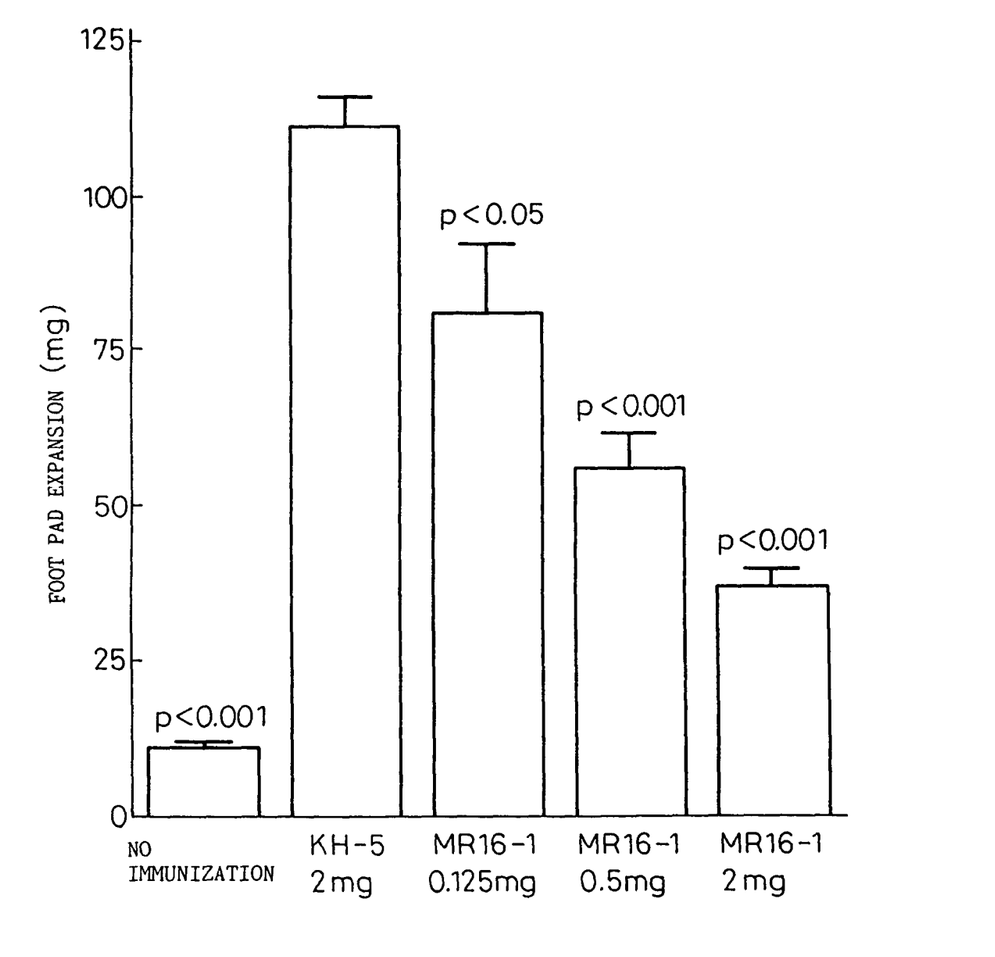
FIG. 1 shows a suppressive action on the mouse delayed-type foot pad edema reaction by MR16-1 after the simultaneous administration of MR16-1 as the sensitization by tubercle bacillus.

MR16-1 antibody at 0.125 mg, 0.5 mg, or 2 mg was intraperitoneally given only once simultaneously with the challenge. The control group received rat IgG (KH-5) having the same isotype and the unsensitized mouse group received physiological saline in a similar manner. The result is shown in FIG. 1.

The one time administration of MR16-1 antibody on the day of challenge inhibited the delayed foot pad edema reaction in a dose-dependent manner.

Reference Example 1

Preparation of Human Soluble IL-6 Receptor

Soluble IL-6 receptor was prepared by the PCR method using a plasmid pBSF2R.236 containing cDNA that encodes IL-6 receptor obtained according to the method of Yamasaki et al., Science (1988) 241, 825-828. Plasmid pBSF2R.236 was digested with a restriction enzyme Sph I to obtain the cDNA of IL-6 receptor, which was then inserted into mp18 (manufactured by Amersham). Using a synthetic oligoprimer designed to introduce a stop codon into the cDNA of IL-6 receptor, a mutation was introduced into the cDNA of IL-6 receptor by the PCR method using the in vitro Mutagenesis System (manufactured by Amersham). The procedure resulted in the introduction of a stop codon to the amino acid at position 345, and gave the cDNA eoncoding soluble IL-6 receptor.

In order to express the cDNA of soluble IL-6 receptor in CHO cells, it was ligated to plasmid pSV (manufactured by Pharmacia) to obtain plasmid pSVL344. The cDNA of soluble IL-6 receptor that was cleaved with Hind III-Sal I was inserted to plasmid pECEdhfr containing the cDNA of dhfr to obtain plasmid pECEdhfr344 that can be expressed in the CHO cells.

Ten μg of plasmid pECEdhfr344 was transfected to a dhfr-CHO cell line DXB-11 (Urland et al., Proc. Natl. Acad. Sci. U.S.A. (1980) 77, 4216-4220) by the calcium phosphate method (Chen et al., Mol. Cell. Biol. (1987) 7, 2745-2751). The transfected CHO cells were cultured in a nucleoside-free a MEM selection medium containing 1 mM glutamin, 10% dialyzed FCS, 100 U/ml penicillin, and 100 μg/ml streptomycin.

The selected CHO cells were screened by the limiting dilution method to obtain a single CHO cell clone. The CHO cell clone was amplified in 20 nM to 200 nM methotrexate (MTX) to obtain a CHO cell line 5E27 that produces human soluble IL-6 receptor. The CHO cell line 5E27 was cultured in an Iscov-modified Dulbecco's medium (IMDM, manufactured by Gibco) containing 5% FBS. The culture supernatant was collected and the concentration of soluble IL-6 receptor in the culture supernatant was determined by ELISA.

Reference Example 2

Preparation of Anti-Human IL-6 Antibody

Ten μg of the recombinant IL-6 (Hirano et al., Immunol. Lett., 17:41, 1988) was immunized to BALB/c mice together with Freund's complete adjuvant, and this was repeated every week until anti-IL-6 antibody could be detected in the serum. Immune cells were extracted from local lymph node and were then fused with a myeloma cell line P3U1 using polyethylene glycol 1500. Hybridomas were selected according to the method of Oi et al. (Selective Methods in Cellular Immunolgy, W. H. Freeman and Co., San Francisco, 351, 1980) that employs the HAT medium, and the hybridoma that produces anti-human IL-6 antibody was established.

The hybridoma that produces anti-human IL-6 antibody was subjected to IL-6 binding assay as follows. Thus, a 96-well microtiter plate made of flexible polyvinyl (manufactured by Dynatech Laboratories, Inc., Alexandria, Va.) was coated with 100 μl of goat anti-mouse Ig (10 μl/ml, manufactured by Cooper Biomedical, Inc., Malvern, Pa.) in 0.1 M carbonate-hydrogen carbonate buffer, pH9.6, overnight at 4° C. Subsequently, the plate was treated with PBS containing 1% bovine serum albumin (BSA) at room temperature for 2 hours.

After washing in PBS, 100 µl of the hybridoma culture supernatant was added to each well, and then was incubated overnight at 4° C. The plate was washed, $^{125}$I-labled recombinant IL-6 was added to each well to a concentration of 2000 cpm/0.5 ng/well, and then radioactivity of each well after washing was determined by a gamma counter (Beckman Gamma 9000, Beckman Instruments, Fullerton, Calif.). Of 216 hybridoma clones, 32 were positive in the IL-6 binding assay. From these clones, stable MH166.BSF2 was finally obtained. Anti-IL-6 antibody MH166 produced by said hybridoma has a subtype of IgG1 κ.

Then, the IL-6-dependent mouse hybridoma clone MH166.BSF2 was used to examine a neutralizing activity with respect to the growth of the hybridoma by MH166. MH166.BSF2 cells were aliquoted to $1 \times 10^4/200$ µl/well, and samples containing MH166 antibody were added thereto, cultured for 48 hours, 15.1 Ci/mM $^3$H-thymidine (New England Nuclear, Boston, Mass.) was added, and the culturing was continued for further 6 hours. The cells were placed on a glass filter paper and were treated by the automatic harvester (Labo Mash Science Co., Tokyo, Japan). As the control, rabbit anti-IL-6 antibody was used.

As a result, MH166 antibody inhibited the incorporation of $^3$H-thymidine of MH166.BSF2 cells iundeced by IL-6 in a dose dependent manner. This revealed that MH166 antibody neutralizes the activity of IL-6.

Reference Example 3

Preparation of Anti-Human IL-6 Receptor Antibody

Anti-IL-6 receptor antibody MT18 prepared by the method of Hirata et al. (J. Immunol., 143, 2900-2906, 1989) was bound to CNBr-activated Sepharose 4B (manufactured by Pharmacia Fine Chemicals, Piscataway, N.J.) according to the attached regimen and IL-6 receptor (Science (1988) 241, 825-828) was purified. A human myeloma cell line U266 was solubilized with 1 mM p-para-aminophenyl methane sulphonyl fluoride hydrochloride (manufactured by Wako Chemicals) containing 1% digitonin (manufactured by Wako Chemicals), 10 mM triethanolamine (pH 7.8) and 0.15 M NaCl (digitonin buffer), and mixed with MT18 antibody bound to Sepharose 4B beads. Then, the beads were washed six times with the digitonin buffer, to prepare the partially purified IL-6 receptor.

BALB/c mice were immunized four times every ten days with the above partially purified IL-6 receptor obtained from $3 \times 10^9$ U266 cells, and then a hybridoma was prepared using a standard method. The hybridoma culture supernatant from the growth-positive well was tested for its activity of binding to IL-6 receptor according to the method described below. $5 \times 10^7$ U266 cells were labeled with $^{35}$S-methionine (2.5 mCi) and were solubilized with the above digitonin buffer. The solubilized U266 cells were mixed with a 0.04 ml volume of MT18 antibody bound to Sepharose 4B beads, and then were washed six times with the digitonin buffer. $^{35}$S-methionine-labeled IL-6 receptor was eluted with 0.25 ml of the digitonin buffer (pH 3.4) and was neutralized in 0.025 ml of 1M Tris (pH 7.4).

0.05 ml of the hybridoma culture supernatant was mixed with 0.01 ml of Protein G Sepharose (manufactured by Pharmacia). After washing, Sepharose was incubated with 0.005 ml $^{35}$S-labeled IL-6 receptor solution prepared-as described above. The immunoprecipitate was analyzed by SDS-PAGE to investigate the hybridoma culture supernatant that reacts with IL-6 receptor. As a result, the reaction positive hybridoma clone PM-1 was established. The antibody produced from the hybridoma PM-1 has a subtype of IgG1κ.

The inhibitory activity of IL-6 binding of the antibody produced by the hybridoma PM-1 to human IL-6 receptor was studied using the human myeloma cell line U266. A human recombinant IL-6 was prepared from *E. coli* (Hirano et al., Immunol. Lett., 17:41, 1988), and was labeled with $^{125}$I using the Bolton-Hunter reagent (New England Nuclear, Boston, Mass.) (Taga, T. et al., J. Exp. Med. (1987) 166, 967). $4 \times 10^5$ U266 cells were cultured with the 70% (v/v) culture supernatant of hybridoma PM-1 together with 14,000 cpm of $^{125}$I-labeled IL-6 in the presence of 100-fold excess of unlabeled IL-6 for one hour at room temperature. Seventy µl of the sample was layered on 300 µl FCS in a 400 µl microfuge polyethylene tube. After centrifugation, the radioactivity of the cell was determined.

The result revealed that the antibody produced by the hybridoma PM-1 inhibits the binding of IL-6 to IL-6 receptor.

Reference Example 4

Preparation of Anti-Mouse IL-6 Receptor Antibody

A monoclonal antibody directed against mouse IL-6 receptor was prepared according to the method described in Saito, et al., J. Immunol. (1993) 147, 168-173.

The CHO cells that produce mouse soluble IL-6 receptor were cultured in the IMDM liquid medium containing 10% FCS. From the culture supernatant, mouse soluble IL-6 receptor was purified using mouse soluble IL-6 receptor RS12 (see Saito, et al., supra) and an affinity column fixed to Affigel 10 gel (Biorad).

The mouse soluble IL-6 receptor (50 µg) thus obtained was mixed with Freund's complete adjuvant, which was then injected to the abdomen of Wistar rats (Japan Charles River). From 2 weeks the animals were boosted with Freund's incomplete adjuvant. On day 45, the rats were sacrificed, and the spleen cells at about $2 \times 10^8$ were fused with $1 \times 10^7$ mouse myeloma cells P3U1 using 50% PEG1500 (Boehringer Mannheim) according to the conventional method, and then were screened by the HAT culture medium.

After the culture supernatant was added to the plate coated with rabbit anti-rat IgG antibody (Cappel), mouse soluble IL-6 receptor was reacted. Subsequently, using rabbit anti-mouse IL-6 receptor antibody and alkaline phosphatase-labeled sheep anti-rabbit IgG, hybridomas producing antibody directed against mouse soluble IL-6 receptor were screend by ELISA. After antibody production was confirmed, the hybridoma clones were subscreened twice to obtain a single hybridoma clone. The clone was designated as MR16-1.

The neutralizing activity of the antibody produced by the hybridoma on signal transduction of mouse IL-6 was examined by $^3$H-thymidine incorporation using MH60.BSF2 cells (Matsuda et al., J. Immunol. (1988) 18, 951-956). To a 96-well plate, MH60.BSF2-cells were prepared at $1 \times 10^4$ cells/200 µl/well. To the plate were added mouse IL-6 and MR16-1 antibody or RS12 antibody at 12.3-1000 ng/ml, and then were cultured at 37° C. and 5% CO2 for 44 hours and then 1 µCi/well of $^3$H-thymidine was added. After 4 hours, the incorporation of $^3$H-thymidine was measured. As a result, MR16-1 antibody suppressed the incorporation of $^3$H-thymidine of the MH60.BSF2 cells.

Thus, it was demonstrated that the antibody produced by the hybridoma MR16-1 inhibits the binding of IL-6 to IL-6 receptor.

INDUSTRIAL APPLICABILITY

In accordance with the present invention, it was shown that IL-6 antagonists such as anti-IL-6 receptor antibody has a suppressive effect on the sensitized T cells. Thus, it was indicated that IL-6 antagonists are useful as a therapeutic agent for multiple sclerosis, uveitis, chronic thyroiditis, delayed hypersensitivity, contact dermatitis, or atopic dermatitis.

Reference to the microorganisms deposited under the Patent Cooperation Treaty, Rule 13-2, and the name of the Depository institute
Depository institute
Name: the National Institute of Bioscience and Human Technology, Agency of Industrial Science and Technology
Address: 1-3, Higashi 1-chome, Tsukuba-shi, Ibaraki, Japan
Microorganism (1)
  Indication: Rat-mouse hybridoma MR16-1
  Deposition number: FERM BP-5875
  Deposition date: Mar. 13, 1997
Microorganism (2)
  Indication: HB 101-pIBIBSF2R
  Deposition number: FERM BP-2232
  Deposition date: Jan. 9, 1989
Microorganism (3)
  Indication: PM1
  Deposition number: FERM BP-2998
  Deposition date: Jul. 12, 1989
Depository organ
Name: National Collection of Industrial and Marine Bacteria Limited
Address: 23 St Machar Drive Aberdeen AB2 IRY
Microorganism (4)
  Indication: *Escherichia coli* DH5α-pPM-k3
  Deposition number: NCIMB 40366
  Deposition date: Feb. 12, 1991
Microorganism (5)
  Indication: *Escherichia coli* DH5α-pPM-h1
  Deposition number: NCIMB 40362
  Deposition date: Feb. 12, 1991

The invention claimed is:

1. A method for treating a disease mediated by a sensitized T cell, which comprises:
  (a) providing a pharmaceutical composition comprising an antibody that binds to interleukin-6 (IL-6) receptor (IL-6R) and inhibits the binding of IL-6 to IL-6R to block the transduction of the biological activity of IL-6 into the cell, and a pharmaceutically acceptable carrier; and
  (b) systemically administering to a patient in need thereof a therapeutically effective amount of the pharmaceutical composition,
wherein the disease mediated by the sensitized T cell is uveitis, chronic thyroiditis, delayed hypersensitivity, contact dermatitis, or atopic dermatitis.

2. The method according to claim 1, wherein the antibody directed against the IL-6R is a recombinant antibody.

3. The method according to claim 1, wherein the antibody directed against the IL-6 receptor is a monoclonal antibody.

4. The method according to claim 3, wherein the monoclonal antibody directed against the IL-6R is a recombinant monoclonal antibody.

5. The method according to claim 3, wherein the monoclonal antibody is a recombinant antibody comprising a constant region of a human antibody.

6. The method according to claim 3, wherein the patient is human and wherein the monoclonal antibody is directed against the human IL-6 receptor.

7. The method according to claim 6, wherein the monoclonal antibody is a PM-1 antibody and the patient in need thereof is a human.

8. The method according to claim 6, wherein the monoclonal antibody comprises a constant region of a human antibody.

9. The method according to claim 6, wherein the monoclonal antibody is a chimeric or humanized antibody directed against the IL-6 receptor.

10. The method according to claim 9, wherein the monoclonal antibody is a chimeric or a humanized PM-1 antibody.

11. The method of claim 1, wherein the pharmaceutical composition is administered by intravenous injection.

12. The method of claim 1, wherein the pharmaceutical composition is administered by subcutaneous injection.

13. The method of claim 1, wherein the disease mediated by a sensitized T cell is uveitis.

14. The method of claim 1, wherein the disease mediated by a sensitized T cell is chronic thyroiditis.

15. The method of claim 1, wherein the disease mediated by a sensitized T cell is delayed hypersensitivity.

16. The method of claim 1, wherein the disease mediated by a sensitized T cell is contact dermatitis.

17. The method of claim 1, wherein the disease mediated by a sensitized T cell is atopic dermatitis.

18. A method for ameliorating atopic dermatitis comprising:
  (a) providing a pharmaceutical composition comprising (i) an antibody that binds to interleukin-6 (IL-6) receptor (IL-6R) and inhibits the binding of IL-6 to IL-6R to block the transduction of the biological activity of IL-6 into the cell, and (ii) a pharmaceutically acceptable carrier; and
  (b) systemically administering to a patient in need thereof a therapeutically effective amount of the pharmaceutical composition.

19. The method of claim 18, wherein the pharmaceutical composition is administered by intravenous injection.

20. The method of claim 18, wherein the pharmaceutical composition is administered by subcutaneous injection.

* * * * *